United States Patent [19]
Bolinger

[11] Patent Number: 6,037,506
[45] Date of Patent: Mar. 14, 2000

[54] HYDROFORMYLATION PROCESS

[75] Inventor: Cornelius Mark Bolinger, Sugar Land, Tex.

[73] Assignee: Shell Oil Company, Houston, Tex.

[21] Appl. No.: 09/156,851

[22] Filed: Sep. 18, 1998

[51] Int. Cl.$^7$ .................................................. C07C 27/20
[52] U.S. Cl. ........................... 568/909; 560/233; 568/454
[58] Field of Search ................................. 568/909, 454; 560/233

[56] References Cited

U.S. PATENT DOCUMENTS

| | | | |
|---|---|---|---|
| 3,880,940 | 4/1975 | Baer et al. | 260/639 |
| 3,929,898 | 12/1975 | Nienburg et al. | 260/604 |
| 3,941,848 | 3/1976 | Kummer et al. | 260/604 |
| 4,229,381 | 10/1980 | Ogata | 568/454 |
| 4,709,105 | 11/1987 | Grenacher et al. | 568/883 |
| 4,723,036 | 2/1988 | Kitamura et al. | 560/238 |
| 5,436,356 | 7/1995 | Drent et al. | 554/129 |
| 5,488,174 | 1/1996 | Drent et al. | 568/454 |

FOREIGN PATENT DOCUMENTS 1127965  9/1968  United Kingdom .

*Primary Examiner*—Michael L. Shippen

[57] ABSTRACT

A process is presented in which ethylenically unsaturated compounds are reacted with carbon monoxide and hydrogen to form reaction products. The reactants are contacted in the presence of a catalyst system made by combining:

(a) a source of palladium, platinum, or nickel, (b) a bidentate ligand of the formula $R_1R_2M_1RM_2R_3R_4$ in which $M_1$ and $M_2$ independently may be phosphorus, arsenic, or antimony atoms, R is a bivalent organic bridging group and $R_1$, $R_2$, $R_3$ and $R_4$ are unsubstituted or substituted aliphatic groups, wherein one or more combinations of $R_1$, $R_2$, $R_3$, and $R_4$ form a bivalent cyclic group, and (c) an acid, and a promoter which is a formate, formic acid, or formic acid forming reagent provided that it is not an orthoformate.

9 Claims, No Drawings

HYDROFORMYLATION PROCESS

BACKGROUND OF THE INVENTION

This invention relates to the hydroformylation of unsaturated hydrocarbons. In hydroformylation processes, carbon monoxide and hydrogen are reacted with an olefin to produce the corresponding hydroxymethyl-substituted or formyl-substituted derivative of the olefin. These processes are of great industrial importance in converting olefins, to aldehydes and alcohols. Other products such as esters, acids, and amides can generally be prepared in analogous processes by adding the carbonyl moiety or the hydroxymethyl moiety to one of the carbon atoms situated at a double bond of the olefin.

U.S. Pat. No. 5,488,174 describes a hydroformylation process which employs a catalyst system comprising a source of palladium and a bidentate ligand of the formula $R_1R_2M_1RM_2R_3R_4$ in which $M_1$ and $M_2$ independently may be phosphorus, arsenic, or antimony atoms. R is a bivalent organic bridging group and $R_1$, $R_2$, $R_3$ and $R_4$ are unsubstituted or substituted aliphatic groups. One or more combinations of $R_1$, $R_2$, $R_3$, and R4 form a bivalent cyclic group. These ligands can include, for example, a 1,2-bis (phosphabicyclononyl)ethane.

Generally, when such a process is used in hydroformylation, a halide salt such as NaCl or NaI is used as promoter and a cosolvent such as sulfalone is added. The promoters generally improve the reaction rate, reduce paraffin make, and increase the linearity of products, relative to the same process without the addition of promoter. These processes have high selectivity and conversion.

U.S. Pat. No. 5,436,356 describes a carbonylation process using a catalyst system of the type described above. The patent further describes the use of drying agents in such processes with trimethyl orthoformate being the preferred drying agent. Such drying agents react with water to form an alcohol (e.g., methanol) and an ester (e.g. methyl formate). This ensures that the desired ester is produced instead of the related acid. Thus, such an addition of trimethyl orthoformate is useful in carbonylation processes when the presence of water is to be minimized. Such agents would not find utility in processes deliberately conducted in the presence of water.

It is well known that halides such as chlorine can damage or destroy metal reactors. It is desirable to employ a hydroformylation process which achieves the same or similar performance as those described above without deleteriously affecting the reactors or vessels used.

SUMMARY OF THE INVENTION

A process for producing alcohols or other hydroformylation products is presented in which an olefinic feed is reacted with hydrogen and carbon monoxide in the presence of a catalyst system made by combining:

(a) a source of palladium, platinum, or nickel,
(b) a bidentate ligand of the formula $R_1R_2M_1RM_2R_3R_4$ in which $M_1$ and $M_2$ independently may be phosphorus, arsenic, or antimony atoms, R is a bivalent organic bridging group and $R_1$, $R_2$, $R_3$ and $R_4$ are unsubstituted or substituted aliphatic groups, wherein one or more combinations of $R_1$, $R_2$, $R_3$, and $R_4$ form a bivalent cyclic group, and
(c) a promoter comprising a formate, formic acid, or formic acid forming reagent provided that such component is not an orthoformate.

In another aspect of this invention, the cyclic groups of the bidentate ligand have at least 5 ring atoms in which the two free valencies are linked to $M_1$ or $M_2$. The combinations include $R_3$ together with $R_4$, R1 together with $R_2$, and $R_1$ together with $R_2$ and $R_3$ together with R4.

In yet another aspect of this invention, hydroformylation products are produced by reacting olefinic feed with hydrogen and carbon monoxide in the presence of a catalyst comprised of a source of palladium and diphosphine ligand in the additional presence of water and a promoter comprising formate, formic acid or formic acid forming reagent wherein the promoter is separated from the hydroformylation products by aqueous extraction at a pH of at least 8.

DETAILED DESCRIPTION OF THE INVENTION

The process of this invention is practiced by contacting a feed stream comprising an ethylenically unsaturated compound, carbon monoxide, and hydrogen with a catalyst in the presence of a promoter under hydroformylation conditions.

The ethylenically unsaturated compounds used as starting materials are preferably $C_{2-24}$ molecules. They may comprise one or more double bonds per molecule. Substituted olefins such as unsaturated carboxylic acids and esters of such acids such as allyl acetate are useful in this regard. Mid to lower alkenes are especially useful olefinic feedstocks for the process of this invention. More particularly, $C_{4-20}$ α-alkenes feeds are desired. The process is useful in converting ethene to propionaldehyde or a mixture of propionaldehyde and n-propanol. Where alcohols are additionally included in the feedstock, esters are produced. Propionates are particularly desirable products. Most preferably, ethene and methanol or butanol feeds are used to produce methyl propionate and/or butyl propionate respectively. If desired, branched olefins such as trimer or isomeric butene dimers may be used. In such instances the products will, of course, contain branched structures as well.

Carbon monoxide and hydrogen may be supplied in equimolar or non-equimolar amounts. Ranges of about 3:1 to 1:3 moles of $CO/H_2$ are useful. Preferably, CO and $H_2$ are supplied in a substantially equimolar amount.

The catalyst system is comprised of a palladium group metal, ligand, and catalyst promoter. The source of palladium, platinum, or nickel and the method of making and using the bidentate ligand is described in U.S. Pat. No. 5,488,174 incorporated herein by reference. The palladium cations may originate from salts. Salts derived from nitric acid have been found useful in this regard. Additionally, sulfuric acid, and sulfonic acids, such as p-toluenesulfonic acid, methanesulfonic acid or trifluoromethanesulfonic acid can be used as palladium cation sources. Preferably, a palladium salt of a carboxylic acid is used such as acetic acid, trifluoroacetic acid, or propionic acid.

It is also possible to employ a palladium, platinum, or nickel source such as the metallic element itself or a zero valence noble metal complex. Such a zero valence complex can be used with carbon monoxide, for example. This would require the presence of a protonic acid.

In the bidentate ligands of the catalyst system, it is preferred that $M_1$ and $M_2$ are both phosphorus atoms. R is preferably a bivalent organic bridging group, containing from 1 to 10 atoms in the bridge. More preferably, R represents an alkene group containing from 1 to 4 atoms in the bridge. In general the bridging group consists of carbon and hydrogen atoms, but it may also comprise a carbon chain, interrupted by a heteroatom, such as an oxygen or silicon atom. It is most preferred that R is a $C_2$ alkene.

The cyclic groups formed by $R_1$ together with $R_2$ and/or $R_3$ together with $R_4$ have at least 5 ring atoms. More preferred embodiments have 6 to 9 ring atoms. Ring systems having 7 or 8 carbon atoms are even more preferred. These ring atoms are generally carbon atoms but cyclic groups containing 1 or 2 heteroatoms in the ring such as oxygen or nitrogen atoms are not precluded. The two free valencies may occur at adjacent carbon ring atoms or at two carbon atoms which are further apart. Examples of suitable cyclic groups include but are not limited to: 1,2-cyclooctylene, 1,3-cyclooctylene, 1,4-cyclooctylene, 1,5-cyclooctylene, 1,4-cyclohexylene, 1,3-cycloheptylene and 1,4-cycloheptylene groups.

Mixtures of bidentate ligands may also be used. Here, $R_1$ together with $R_2$ may represent various cyclic groups while $R_3$ and $R_4$ represent either non-cyclic aliphatic groups. Alternatively, $R_3$ together with $R_4$ may represent cyclic groups which may be the same as or different from the cyclic group represented by $R_1$ and $R_2$. Examples of suitable mixtures of bidentate ligands are 1,2-bis(9-phosphabicyclo[3.3.1.]nonyl)ethane and 1,2-bis(9-phosphabicyclo[4.2.1.]nonyl)ethane; 1,3-bis(9-phosphabicyclo[3.3.1 ]nonyl)propane and 1,3-bis(9-phosphabicyclo[4.2.1 ]nonyl)propane; 1-dialkylphosphino-2-P-(9-phosphabicyclo[3.3.1]nonyl)ethane and 1-dialkylphosphino-2-P-(9-phosphabicyclo[4.2.1.]nonyl)ethane.

In embodiments in which either $R_1$ and $R_2$, or $R_3$ and $R_4$ do not represent a bivalent cyclic group, they can be optionally substituted alkyl or monovalent cycloalkyl groups. $C_{1-6}$ alkyls and C 5-10 cycloalkyls are preferred. Examples of suitable alkyl groups are methyl, ethyl or butyl groups. Cyclohexyl or cyclooctyl groups are preferred cycloalkyls. The catalysts used in this invention are prepared in-situ by combining the source of palladium, the bidentate ligand, the acid (such as methanesulfonic acid), and a catalyst carrier solvent into the reactor in which the process will be conducted. Alternatively, the catalyst can be prepared separately and then added to a reactor with the addition of the reactants, water, and promoter. The ligand can be prepared to methods which are now well known such as those described in British Patent Specification No. 1,127,965.

The ratio of number of moles of ligands per gram atom of palladium is preferably in the range of from 0.5 to 10. The most preferred range is from 1 to 3 moles of ligand per gram atom of palladium.

The quantity of catalyst used can vary within wide limits. Usually, about $10^{-8}$ to about $10^{-1}$, preferably about $10^{-7}$ to about $10^{-2}$ gram atoms of platinum, palladium, or nickel metal per molecule of ethylenically unsaturated compound are used. The amounts of the participants in the catalyst system are conveniently selected such that per gram atom of platinum, palladium, or nickel metal, from about 0.5 to about 10, preferably from about 1 to about 6 moles of bidentate ligand are used, from about 0.5 to about 15, preferably from about 1 to about 8 moles of anion source or a complex anion source.

It is possible to hydroformylate an olefin by merely exposing the feed stock to the catalyst system described above under well known process conditions. However, without the presence of a promoter, conversion rates can be less than fifty percent of those obtained when a promoter is present.

The promoters of this invention include formates, formic acid, or formic acid forming reagents. Alkyl formates are preferred. $C_{1-20}$ alkyl formates are more preferred and butyl formate is the most preferred promoter. However, esters, amides, salts (in the presence of a protic acid), anhydrides, or other formic acid derivatives which can dissociate, react, or otherwise transform in situ to form formic acid can be useful in this regard. Orthoesters such as trimethylorthoformate are not within the scope of this invention as their primary purpose would otherwise entail dehydration. In the process of the present invention, water is deliberately added in significant quantity thus precluding orthoformates as useful promoters.

When formic acid is used, any addition of at least 0.05 wt % (based on the weight of reactor) promoter to the catalyst and feed will improve the process. Preferably, between about 0.05 and 1.5 promoter are added. It is more preferred that at least 0.3 wt % (based on the weight of reactor charge) be employed. It is most preferred that between about 0.4 and 1.4 wt % (based on the weight of reactor charge) be added. When promoter is added in the amounts indicated above, conversions of between about 86% and 95% are possible at 105° C. and paraffin make is negligible (less than about 2 % mole based on converted olefin). When skilled in the art will readily appreciate the quantities attained when the basis for calculating weight percents is a promoter other than formic acid.

The hydroformylation can be carried out at moderate reaction conditions. Typically, the reactor is heated to the desired temperature then charged with alcohol reactant, water (typically between about 1%wt and 3 %wt based on the weight of reactor charge) and promoter. Catalyst is then added to the reactor followed by the addition of hydrogen and carbon monoxide. Olefinic reactant is typically added next and the reaction is initiated. As one skilled in the art will readily appreciate, this scheme is flexible and may carried out following different sequences if desired. However, it is preferred that the catalyst is preformed in any such scheme. Temperatures in the range of 50° C. to 160° C. are recommended. Preferred temperature are in the range of 70° C. to 130° C. Reaction pressures in the range of 5 bar to about 100 bar are preferred but lower or higher pressures may be selected.

The hydroformylation reaction may be carried out in the additional presence of a solvent. Suitable solvents include ethers such as 2,5,8-tiroxanonane (diglyme), diethyl ether and anisole, and $C_{4-10}$ alcohols such as butanol, ocatanol or ethylhexanol, or in general terms, the alcohol of the same composition as the alcohol produced in the present process.

The promoters of this invention can be readily removed from product liquors. Thus, in addition to providing a promoter which avoids the deleterious metallurgical effects of halide promoters, the promoters of this invention provide an economic system. In the preferred scheme for the removal of formates, the liquor leaving the reactor is directed to a catalyst separation process. This can be comprised of a series of bubble columns. The liquor less the catalyst is then degassed to remove hydrogen and carbon monoxide. The product of these separations is then fed to a saponification section where it is exposed a stoichiometric excess of a strong inorganic base such as NaOH. Other alternatives include separating formates and related products via distillation.

The invention will be illustrated by the following non-limiting examples.

EXAMPLE 1

A 500 mL autoclave was charged with 0.76 mmol palladium (II)acetate, 1.07 mmol of a mixture of 1,2-bis(9- phosphabicyclononyl)ethane, 20.2 mL of anisole (as solvent), 0.45 mL methanesulfonic acid (MSA), 4.80 mL water, 7.91 mL butyl formate (as promoter), and 156 mL octene, 83 ml isononynol. The autoclave was flushed with an equimolar mixture of carbon monoxide and hydrogen pressurized to a total pressure of 50 bar. The autoclave was then sealed and the mixture was heated to 110° C. The reaction was continued for 8 hours and subsequently the reaction mixture was cooled to room temperature and the pressure released. 163 g of nonyl alcohol product was produced (94% conversion of starting material). The reaction rate was about 0.36 hr$^{-1}$. There was no noticeable paraffin make. This example illustrates that the use of a formic acid derivative as a promoter results in high conversion/high selectivity reactions with excellent reaction rates.

EXAMPLE 2 (Comparative)

Example 1 was repeated without the addition of butyl formate. 78 g of nonyl alcohol product was produced. The reaction rate was about 0.19 hr$^{-1}$. There was 2.15% m paraffin make.

EXAMPLE 3 (Prophetic)

Formic acid is treated to remove substantially all impurities present. A 500 mL autoclave is charged with 0.76 mmol palladium (II)acetate, 1.07 mmol of a mixture of 1,2-bis(9-phospha-bicyclononyl)ethane, 20.2 mL of anisole (as solvent), 0.45 mL methanesulfonic acid (MSA), 4.80 mL water, 2.72 mL glacial (96%w) formic acid (as promoter), and 156 mL octene. The autoclave is flushed with an equimolar mixture of carbon monoxide and hydrogen pressurized to a total pressure of 50 bar. The autoclave is then sealed and the mixture is heated to 105° C. The reaction is continued to complete octene conversion and subsequently the reaction mixture is cooled to room temperature and the pressure released.

147 g of nonyl alcohol product is produced (100% conversion of starting material). The reaction rate is about 0.36 hr$^{-1}$. There is 2% m paraffin make and 1% m heavy ends make.

This example illustrates that the use of formic acid as a promoter results in high conversion/high selectivity reactions with excellent reaction rates.

What is claimed is:

1. A process comprising contacting ethylenically unsaturated compounds with carbon monoxide and hydrogen reactants to form reaction products wherein said reactants are contacted in the presence of a catalyst system made by combining:
   (a) a source of palladium, platinum, or nickel,
   (b) a bidentate ligand of the formula $R_1R_2M_1RM_2R_3R_4$ in which $M_1$ and $M_2$ independently may be phosphorus, arsenic, or antimony atoms, R is a bivalent organic bridging group and $R_1$, $R_2$, $R_3$ and $R_4$ are unsubstituted or substituted aliphatic groups, wherein one or more combinations of $R_1$, $R_2$, $R_3$, and $R_4$ form a bivalent cyclic group, and
   (c) an acid,
and a promoter comprising a formate, formic acid, or formic acid forming reagent provided that said promoter is not an orthoformate.

2. The process of claim 1 wherein the cyclic groups of the bidentate ligand have at least 5 ring atoms in which the two free valencies are linked to $M_1$ or $M_2$. The combinations include $R_3$ together with $R_4$, R1 together with $R_2$, and $R_1$ together with $R_2$ and $R_3$ together with $R_4$.

3. The process of claim 1 conducted in the additional presence of water.

4. The process of claim 1 wherein said promoter is formic acid or a an ester of formic acid.

5. The process of claim 1 wherein said promoter is butyl formate.

6. The process of claim 1 wherein said olefinic feed comprises octene.

7. A process for producing hydroformylation products by reacting olefinic feed with hydrogen and carbon monoxide in the presence of a catalyst comprised of a source of palladium and diphosphine ligand in the additional presence of water and a promoter comprising formate, formic acid or formic acid forming reagent provided that said promoter is not an orthoformate.

8. The process of claim 1 wherein between about 0.05 wt % and 1.5 wt % promoter is added to said feed, hydrogen, carbon monoxide, and catalyst (based on equivalent weight of formic acid in the total weight of reactants and catalyst).

9. The process of claim 1 wherein said alkyl formate is a $C_{1-20}$ ester.

* * * * *